(12) United States Patent
Karami et al.

(10) Patent No.: US 10,273,206 B2
(45) Date of Patent: *Apr. 30, 2019

(54) TROMETHAMINE SALT OF BIMATOPROST ACID IN CRYSTALLINE FORM 1, METHODS FOR PREPARATION, AND METHODS FOR USE THEREOF

(71) Applicant: ALLERGAN, INC., Irvine, CA (US)

(72) Inventors: Thomas K. Karami, Aliso Viejo, CA (US); Scott W. Smith, Mission Viejo, CA (US); Fiona Dubas-Fisher, Ely (GB); Adrian St. Clair Brown, Ely (GB)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/318,402

(22) Filed: Jun. 27, 2014

(65) Prior Publication Data

US 2015/0376125 A1    Dec. 31, 2015

(51) Int. Cl.
*A61K 31/215* (2006.01)
*C07C 405/00* (2006.01)
*C07C 215/10* (2006.01)

(52) U.S. Cl.
CPC .......... *C07C 405/00* (2013.01); *C07C 215/10* (2013.01); *C07B 2200/13* (2013.01); *C07C 2601/10* (2017.05)

(58) Field of Classification Search
CPC .................................................. A61K 31/205
USPC ......................................................... 514/530
See application file for complete search history.

(56) References Cited

U.S. PATENT DOCUMENTS

| 4,556,413 | A | 12/1985 | Frater et al. |
| 8,629,185 | B2 | 1/2014 | Ambrus et al. |
| 2009/0163596 | A1 | 6/2009 | Gutman et al. |
| 2010/0105775 | A1 | 4/2010 | Delong et al. |
| 2014/0187636 | A1 | 7/2014 | Wu et al. |
| 2014/0187637 | A1 | 7/2014 | Karami et al. |

FOREIGN PATENT DOCUMENTS

| EP | 0109575 A2 | | 5/1984 |
| WO | 9800100 | | 1/1998 |
| WO | WO 98/00100 | * | 8/1998 |
| WO | 2011063276 A1 | | 5/2011 |
| WO | 2012164324 | | 12/2012 |
| WO | 2014106194 | | 7/2014 |
| WO | 2014106194 A1 | | 7/2014 |
| WO | 2014106204 | | 7/2014 |
| WO | 2014106204 A1 | | 7/2014 |

OTHER PUBLICATIONS

U.S. Appl. No. 14/136,914, 2012.
U.S. Appl. No. 14/137,447, 2013.
Bito, L. Z., Biological Protection with Prostaglandins, Cohen, M. M., ed., Boca Raton, Fla. CRC Press Inc., 1985, pp. 231-252.
Bito, L.Z., Gluacoma: Applied Pharmacology in Medical Treatment, Drance, S.M., et a l. eds. New York, N.Y. Grune & Stratton, 1984, pp. 477-505.
Starr, M.S., Further Studies on the Effect of Prostaglandin on Intraocular Pressure in the Rabbit, Ex. Eye Res. (1971), 11, 170-177.
International Search Report & Written Opinion mailed on Feb. 25, 2015 for PCT/US2014/044658 filed on Jun. 27, 2014 in the name of Allergan, Inc.
International Search Report & Written Opinion mailed on Apr. 8, 2014 for PCT/US2013/078356 filed on Dec. 30, 2013 in the name of Allergan, Inc.
Non-Final Office Action issued on Mar. 24, 2015 for U.S. Appl. No. 14/137,447 filed on Dec. 20, 2013, in the name of Thomas K. Karami et al.
Restriction Requirement issued on Jan. 15, 2015 for U.S. Appl. No. 14/137,447 filed on Dec. 20, 2013, in the name of Thomas K. Karami et al.

* cited by examiner

*Primary Examiner* — Barbara P Badio
(74) *Attorney, Agent, or Firm* — Jonathan Bass

(57) ABSTRACT

The present invention provides tromethamine salt of (Z)-7-[3,5-Dihydroxy-2-((E)-3-hydroxy-5-phenyl-pent-1-enyl)-cyclopentyl]-hept-5-enoic acid in crystalline Form 1 and amorphous form. This compound is may also be referred to as "tromethamine salt of bimatoprost acid." The invention crystalline form is useful for solid ocular implant or topical formulations, utilized in the treatment of various ocular conditions, such as, for example, ocular hypertension.

2 Claims, 8 Drawing Sheets

TROMETHAMINE SALT OF BIMATOPROST ACID IN CRYSTALLINE FORM 1, METHODS FOR PREPARATION, AND METHODS FOR USE THEREOF

FIELD OF THE INVENTION

The present invention relates generally to tromethamine salt of bimatoprost acid and its crystalline form (Form 1) and its amorphous form. The present invention further relates to methods for its preparation and to methods for treating disorders associated with ocular hypertension, hair growth, and fat reduction.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical beta-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. Exp. Eye Res. 1971, 11, pp. 170-177; Bito, L. Z. Biological Protection with Prostaglandins Cohen, M. M., ed., Boca Raton, Fla. CRC Press Inc., 1985, pp. 231-252; and Bito, L. Z., Applied Pharmacology in the Medical Treatment of Glaucomas Drance, S. M. and Neufeld, A. H. eds., New York, Grune & Stratton, 1984, pp. 477-505). Such prostaglandins include $PGF_{2\alpha}$, $PGF_{1\alpha}$, $PGE_2$, and certain lipid-soluble esters, such as $C_1$ to $C_5$ alkyl esters, e.g., 1-isopropyl ester, of such compounds.

Other uses of bimatoprost include use in hair growth, including scalp hair, eyelashes, and eyebrows. Bimatoprost has also shown promise in localized fat reduction and inhibition of adipocyte differentiation.

Prostaglandins tend generally to occur in the form of oils or gums. Solid forms of some prostaglandins are known in the art. The solid forms may be prone to form change upon solid state manufacturing processes, such as granulation, tablet compression and hot melt extrusion. For example, a solid form of a prostaglandin may take the form of an oil or gum during or after a granulation, tablet compression, or extrusion step.

It is known that many drug compounds exist in two or more crystalline forms, referred to as polymorphs. These polymorphs of the same molecule have identical chemical properties but may exhibit different physical properties, such as melting point, solubility, hardness, etc.

Bimatoprost is known to occur in the solid form. US 2009/0163596 discloses bimatoprost crystalline Form I having a characteristic melting point range of 62-64° C. WO 2011/063276 A1 and U.S. Pat. No. 8,629,185 B2 disclose crystalline bimatoprost polymorph II having an endothermic melting onset at about 70.9° C. and a peak at 74.5° C. in its DSC profile. WO 2012/164324 A1 discloses bimatoprost crystal Form II with a melting point range of 72-78° C. U.S. patent application Ser. No. 14/136,914 discloses crystalline forms of bimatoprost acid, with melting temperatures of 64.2° C. (crystalline Form 1) and 66.4° C. (crystalline Form 2), respectively. U.S. patent application Ser. No. 14/136,914 also discloses that some bimatoprost polymorphs convert to an amorphous material after hot melt extrusion.

Preparation of amino acid salts of prostaglandin free acids are reported by DeLong et al. (see US 2010/0105775 A1). DeLong et al. teach that suitably, the salts have a melting point of at least about 35° C., or at least about 50° C.

When a drug compound exists in two or more crystalline forms, or polymorphs, the danger exists of less soluble polymorphic forms precipitating from a solution made from another more soluble but less stable form. The formation of crystals in an ophthalmic solution can cause serious injury to the eye. In addition, precipitation of the drug substance may cause an apparent reduction in potency and bioavailability of the product. Therefore it is important to formulate ocular solutions with drug concentrations below the equilibrium solubility of the thermodynamically most stable polymorph of the drug.

A salt form of a prostaglandin may exhibit desirable solid state properties, such as high melting temperature and high crystallinity. Such properties may be advantageous with respect to manufacturing, stability, and/or solubility. Such a salt form may tolerate solid dosage formulation processes such as granulation, tablet compression and hot melt extrusion.

There is a need for solid state prostaglandins, in particular bimatoprost, with desirable physical properties, including high melting temperature and high crystallinity, which may provide suitable stability, solubility, and tolerability to solid dosage formulation processes.

SUMMARY OF THE INVENTION

The present invention provides tromethamine salt of bimatoprost acid ((Z)-7-[3,5-Dihydroxy-2-((E)-3-hydroxy- 5-phenyl-pent-1-enyl)-cyclopentyl]-hept-5-enoic acid) in its crystalline form (Form 1) and amorphous form. This compound may also be referred to as "tromethamine salt of bimatoprost acid," "bimatoprost acid tromethamine salt" or "bimatoprost acid TRIS salt." The invention crystalline Form 1 is useful for solid ocular implant formulations, gel formulations and topical ophthalmic compositions, such as topical ophthalmic solutions, microsuspensions and intraocular gel suspensions, which can be utilized in the treatment of various ocular conditions, such as, for example, ocular hypertension and glaucoma. In addition, bimatoprost acid tromethamine salt crystalline Form 1 is useful for solid or semisolid dosage formulations used to treat ocular hypertension and glaucoma. The crystalline Form 1 of tromethamine salt of bimatoprost acid may also be used in dermal solutions, lotions, creams, foams, ointments, gels, and suspensions, including gel suspension, micro-suspensions, or nano-suspension formulations, for example, for the treatment of hair growth (eyelash, eyebrow, scalp) and for localized fat reduction.

The invention amorphous form is useful for solid ocular implant formulations, gel formulations and topical ophthalmic compositions, such as topical ophthalmic solutions, microsuspensions and intraocular gel suspensions, which can be utilized in the treatment of various ocular conditions, such as, for example, ocular hypertension and glaucoma. In addition, bimatoprost acid tromethamine salt amorphous form is useful for solid or semisolid dosage formulations used to treat ocular hypertension and glaucoma. The amorphous form of tromethamine salt of bimatoprost acid may also be used in dermal solutions, lotions, creams, foams, ointments, gels, and suspensions, including gel suspension, micro-suspensions, or nano-suspension formulations, for example, for the treatment of hair growth (eyelash, eyebrow, scalp) and for localized fat reduction.

The present invention provides for pharmaceutical compositions comprising tromethamine salt of bimatoprost acid in crystalline Form 1, amorphous form, or mixtures thereof. The invention provides for pharmaceutical compositions comprising tromethamine salt of bimatoprost acid, wherein the compositions are prepared from the tromethamine salt of bimatoprost acid in crystalline Form 1, amorphous form, or mixtures thereof.

The invention provides for pharmaceutical compositions prepared from the tromethamine salt of bimatoprost acid in crystalline Form 1, wherein the composition is in the solid form. The invention also provides for pharmaceutical compositions prepared from the tromethamine salt of bimatoprost acid in crystalline Form 1, wherein the composition is not in the solid form. In some embodiments, the pharmaceutical composition may be a solution. It is understood that in embodiments of the invention reciting pharmaceutical compositions comprising tromethamine salt of bimatoprost acid in crystalline Form 1, wherein the composition is a solution, that the solution is prepared from tromethamine salt of bimatoprost acid in crystalline Form 1, and that the salt is dissolved in the solution.

In one embodiment, there is provided tromethamine salt of bimatoprost acid ((Z)-7-[3,5-Dihydroxy-2-((E)-3-hydroxy-5-phenyl-pent-1-enyl)-cyclopentyl]-hept-5-enoic acid), having the structure:

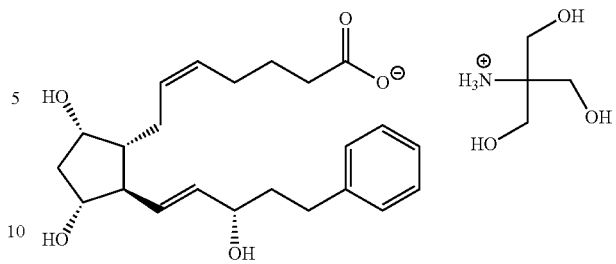

wherein the salt is in crystalline Form 1, having X-ray powder diffraction (XRPD) peaks at the diffraction angles of about: 6.8°, 10.2°, 13.4°, 16.1°, 17.3°, 18.0°, 19.1°, 19.4°, 20.0°, 20.4°, 21.1°, 22.9°, 23.3°, 24.5°, 25.2° and 33.7° of 2-theta (Cu, K-alpha1 radiation with wavelength 1.5406 Å).

In another embodiment, there is provided tromethamine salt of bimatoprost acid of crystalline Form 1 having XRPD peaks at the diffraction angles of: 6.80°, 10.18°, 13.35°, 16.10°, 17.30°, 17.99°, 19.05°, 19.35°, 19.95°, 20.40°, 21.11°, 22.85°, 23.25°, 24.46°, 25.22° and 33.73° of 2-theta (Cu, K-alpha1 radiation with wavelength 1.5406 Å).

In another embodiment, there is provided tromethamine salt of bimatoprost acid of crystalline Form 1 having the XRPD pattern as shown in FIG. 6.

In another embodiment, there is provided tromethamine salt of bimatoprost acid of crystalline Form 1 having a melting enthalpy from about 103.6 J/g to about 119.9 J/g.

In another embodiment, there is provided tromethamine salt of bimatoprost acid of crystalline Form 1 having a melting temperature within the range of about 104-110° C.

In another embodiment, there is provided tromethamine salt of bimatoprost acid of crystalline Form 1 having a melting temperature of about 105° C.

In another embodiment, there is provided tromethamine salt of bimatoprost acid of crystalline Form 1 having a melting temperature of about 105.6° C.

In another embodiment, there is provided tromethamine salt of bimatoprost acid of crystalline Form 1 having a melting temperature of 105.6° C.

In another embodiment, there is provided tromethamine salt of bimatoprost acid in amorphous form having a glass transition temperature (Tg) of about 29° C.

In another embodiment of the invention, there are provided methods for the preparation of tromethamine salt of bimatoprost acid of crystalline Form 1. Such methods include, for example, lyophilization, crystallization in solvent or solvent mixtures by maturation, slurry, cooling, evaporation, and anti-solvent precipitation.

In another embodiment of the invention, there are provided methods for the preparation of tromethamine salt of bimatoprost acid in amorphous form. Such methods include, for example, freeze drying, rotary evaporation, and quenching the melt.

In another embodiment of the invention, there is provided a pharmaceutical composition comprising a therapeutically effective amount of tromethamine salt of bimatoprost acid in crystalline Form 1.

In another embodiment, there is provided a pharmaceutical composition comprising a therapeutically effective amount of tromethamine salt of bimatoprost acid in amorphous form.

In another embodiment, there is provided a pharmaceutical composition wherein the tromethamine salt of bimatoprost acid in crystalline Form 1 is in a pharmaceutically acceptable carrier.

In another embodiment, there is provided a pharmaceutical composition wherein the tromethamine salt of bimatoprost acid in amorphous form is in a pharmaceutically acceptable carrier.

In another embodiment, there is provided a pharmaceutical composition comprising tromethamine salt of bimatoprost acid in crystalline Form 1 as a solid dosage form.

In another embodiment, there is provided a pharmaceutical composition comprising tromethamine salt of bimatoprost acid in amorphous form as a solid dosage form.

In another embodiment, there is provided a pharmaceutical composition comprising tromethamine salt of bimatoprost acid in crystalline Form 1 as a semi-solid dosage form.

In another embodiment, there is provided a pharmaceutical composition comprising tromethamine salt of bimatoprost acid in amorphous form as a semi-solid dosage form.

In another embodiment, there is provided a pharmaceutical composition including a therapeutically effective amount of tromethamine salt of bimatoprost acid in crystalline Form 1, which is a topical formulation for ophthalmic or dermal administration. In some embodiments, the topical formulation is an aqueous or non-aqueous solution.

In another embodiment, there is provided a pharmaceutical composition including a therapeutically effective amount of tromethamine salt of bimatoprost acid in amorphous form, which is a topical formulation for ophthalmic or dermal administration. In some embodiments, the topical formulation is an aqueous or non-aqueous solution.

In one embodiment of the invention, there is provided a pharmaceutical composition comprising a therapeutically effective amount of tromethamine salt of bimatoprost acid in crystalline Form 1 in a pharmaceutically acceptable carrier, such as an ophthalmically acceptable carrier. In a particular embodiment, the composition is suitable for ophthalmic administration. In another embodiment, the composition is suitable for dermal administration.

In another embodiment of the invention, there is provided a pharmaceutical composition comprising a therapeutically effective amount of tromethamine salt of bimatoprost acid in amorphous form in a pharmaceutically acceptable carrier, such as an ophthalmically acceptable carrier. In a particular embodiment, the composition is suitable for ophthalmic administration. In another embodiment, the composition is suitable for dermal administration.

In another embodiment, there is provided a pharmaceutical composition including a therapeutically effective amount of tromethamine salt of bimatoprost acid in crystalline Form 1, which is a dermal formulation. The dermal formulation may be an aqueous or non-aqueous solution, a lotion, an emulsion, a foam, a gel, a cream, an ointment, or a suspension, such as a gel-based micro-suspension or nano-suspension.

In another embodiment, there is provided a pharmaceutical composition including a therapeutically effective amount of tromethamine salt of bimatoprost acid in amorphous form, which is a dermal formulation. The dermal formulation may be an aqueous or non-aqueous solution, a lotion, an emulsion, a foam, a gel, a cream, an ointment, or a suspension, such as a gel-based micro-suspension or nano-suspension.

In another embodiment, there is provided a pharmaceutical composition wherein the tromethamine salt of bimatoprost acid in crystalline Form 1 is in a pharmaceutically acceptable carrier, wherein the pharmaceutically acceptable carrier is an aqueous solution. In some embodiments, the bimatoprost acid in crystalline Form 1 is present in a concentration of 0.01% w/v to 0.1% w/v. In another embodiment, the pharmaceutical composition in crystalline Form 1 is present in a concentration of 0.03% w/v. In yet another embodiment, the tromethamine salt of bimatoprost acid in crystalline Form 1 is at a concentration selected from 0.01, 0.02, 0.03, 0.04. 0.05, 0.06, 0.07, 0.08, 0.09, 0.1, 0.2, 0.3, 0.4. 0.5, 0.6, 0.7, 0.8, 0.9 to 1.0% w/v.

In another embodiment, there is provided a pharmaceutical composition wherein the tromethamine salt of bimatoprost acid in amorphous form is in a pharmaceutically acceptable carrier, wherein the pharmaceutically acceptable carrier is an aqueous solution. In some embodiments, the bimatoprost acid in amorphous form is present in a concentration of 0.01% w/v to 0.1% w/v. In another embodiment, the pharmaceutical composition in amorphous form is present in a concentration of 0.03% w/v. In yet another embodiment, the tromethamine salt of bimatoprost acid amorphous form is at a concentration selected from 0.01, 0.02, 0.03, 0.04. 0.05, 0.06, 0.07, 0.08, 0.09, 0.1, 0.2, 0.3, 0.4. 0.5, 0.6, 0.7, 0.8, 0.9 to 1.0% w/v.

In another embodiment, there is provided a pharmaceutical composition wherein the tromethamine salt of bimatoprost acid in crystalline Form 1 is in a pharmaceutically acceptable carrier, wherein the pharmaceutically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.

In another embodiment, there is provided a pharmaceutical composition wherein the tromethamine salt of bimatoprost acid in amorphous form is in a pharmaceutically acceptable carrier, wherein the pharmaceutically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.

In another embodiment, there is provided a pharmaceutical composition wherein the tromethamine salt of bimatoprost acid in crystalline Form 1 is in a pharmaceutically acceptable carrier, wherein the pharmaceutically acceptable carrier is a gel dosage form.

In another embodiment, there is provided a pharmaceutical composition wherein the tromethamine salt of bimatoprost acid in amorphous form is in a pharmaceutically acceptable carrier, wherein the pharmaceutically acceptable carrier is a gel dosage form.

In another embodiment, there is provided a pharmaceutical composition wherein the tromethamine salt of bimatoprost acid in crystalline Form 1 is in a pharmaceutically acceptable carrier, wherein the composition is a suspension, a dermal solution, or a lotion.

In another embodiment, there is provided a pharmaceutical composition wherein the tromethamine salt of bimatoprost acid in amorphous form is in a pharmaceutically acceptable carrier, wherein the composition is a suspension, a dermal solution, or a lotion.

In another embodiment, there is provided a pharmaceutical composition wherein the tromethamine salt of bimatoprost acid in crystalline Form 1 is in a pharmaceutically acceptable carrier, wherein the composition is a gel suspension, a gel-based micro-suspension, or a nano-suspension.

In another embodiment, there is provided a pharmaceutical composition wherein the tromethamine salt of bimatoprost acid in amorphous form is in a pharmaceutically acceptable carrier, wherein the composition is a gel suspension, a gel-based micro-suspension, or a nano-suspension.

In another embodiment, there is provided a pharmaceutical composition comprising a therapeutically effective amount of tromethamine salt of bimatoprost acid in crystalline Form 1, wherein the composition is used for localized fat reduction.

In another embodiment, there is provided a pharmaceutical composition comprising a therapeutically effective amount of tromethamine salt of bimatoprost acid in amorphous form, wherein the composition is used for localized fat reduction.

In another embodiment, there is provided a pharmaceutical composition comprising a therapeutically effective amount of tromethamine salt of bimatoprost acid in crystalline Form 1, wherein the composition is used to promote hair growth.

In another embodiment, there is provided a pharmaceutical composition comprising a therapeutically effective amount of tromethamine salt of bimatoprost acid in amorphous form, wherein the composition is used to promote hair growth.

In another embodiment, there is provided a pharmaceutical composition comprising a therapeutically effective amount of tromethamine salt of bimatoprost acid in crystalline Form 1, wherein the composition is used to treat elevated intraocular pressure or glaucoma.

In another embodiment, there is provided a pharmaceutical composition comprising a therapeutically effective amount of tromethamine salt of bimatoprost acid in amorphous form, wherein the composition is used to treat elevated intraocular pressure or glaucoma.

In another embodiment, there is provided methods for treating ocular hypertension or glaucoma. Such methods can be performed, for example, by administering to a subject in need thereof a therapeutically effective amount of tromethamine salt of bimatoprost acid in crystalline Form 1 in an ophthalmically acceptable carrier. In some embodiments, the carrier is an emulsion, suspension, or solution. In a particular embodiment, the solution is a topical ophthalmic solution administered as eye drops.

In another embodiment, there is provided methods for treating ocular hypertension or glaucoma. Such methods can be performed, for example, by administering to a subject in need thereof a therapeutically effective amount of tromethamine salt of bimatoprost acid in amorphous form in an ophthalmically acceptable carrier. In some embodiments, the carrier is an emulsion, suspension, or solution. In a particular embodiment, the solution is a topical ophthalmic solution administered as eye drops.

In another embodiment, there is provided a method for treating ocular hypertension comprising administering to a subject in need thereof a therapeutically effective amount of tromethamine salt of bimatoprost acid in crystalline Form 1 in an ophthalmically acceptable carrier. In a particular embodiment of the method, the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof. In yet another embodiment of the method, the tromethamine salt of bimatoprost acid in crystalline Form 1 is dosed at least once a day. In another embodiment, Form 1 is dosed once a day.

In another embodiment, there is provided a method for treating ocular hypertension comprising administering to a subject in need thereof a therapeutically effective amount of tromethamine salt of bimatoprost acid in amorphous form in an ophthalmically acceptable carrier. In a particular embodiment of the method, the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof. In yet another embodiment of the method, the tromethamine salt of bimatoprost acid in crystalline Form 1 is dosed at least once a day. In another embodiment, Form 1 is dosed once a day.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

It is to be understood that "(Z)-7-[3,5-Dihydroxy-2-((E)-3-hydroxy-5-phenyl-pent-1-enyl)-cyclopentyl]-hept-5-enoic acid" and "bimatoprost acid" refer to the same compound and may be used interchangeably throughout. Bimatoprost acid has the following structure:

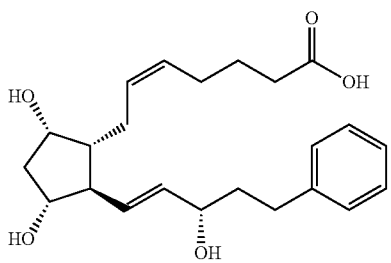 [SMILES: O=C(O)CCC/C=C\C[C@@H]1[C@@H](/C=C/[C@@H](O)CCc2ccccc2)[C@H](O)C[C@@H]1O]

In addition, "tromethamine salt of (Z)-7-[3,5-Dihydroxy-2-((E)-3-hydroxy-5-phenyl-pent-1-enyl)-cyclopentyl]-hept-5-enoic acid" and "tromethamine salt of bimatoprost acid," "bimatoprost acid tromethamine salt" and "bimatoprost acid TRIS salt" refer to the same compound and may be used interchangeably throughout. Tromethamine salt of bimatoprost acid has the structure:

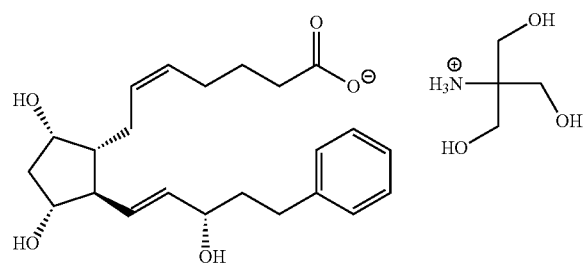 [SMILES: O=C([O-])CCC/C=C\C[C@@H]1[C@@H](/C=C/[C@@H](O)CCc2ccccc2)[C@H](O)C[C@@H]1O ; [NH3+]C(CO)(CO)CO]

In addition, it is to be understood that "crystalline form" and "polymorphic form" and ("Form 1") may be used interchangeably throughout the specification.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

The present invention provides tromethamine salt of bimatoprost acid in crystalline Form 1.

Figure 6:
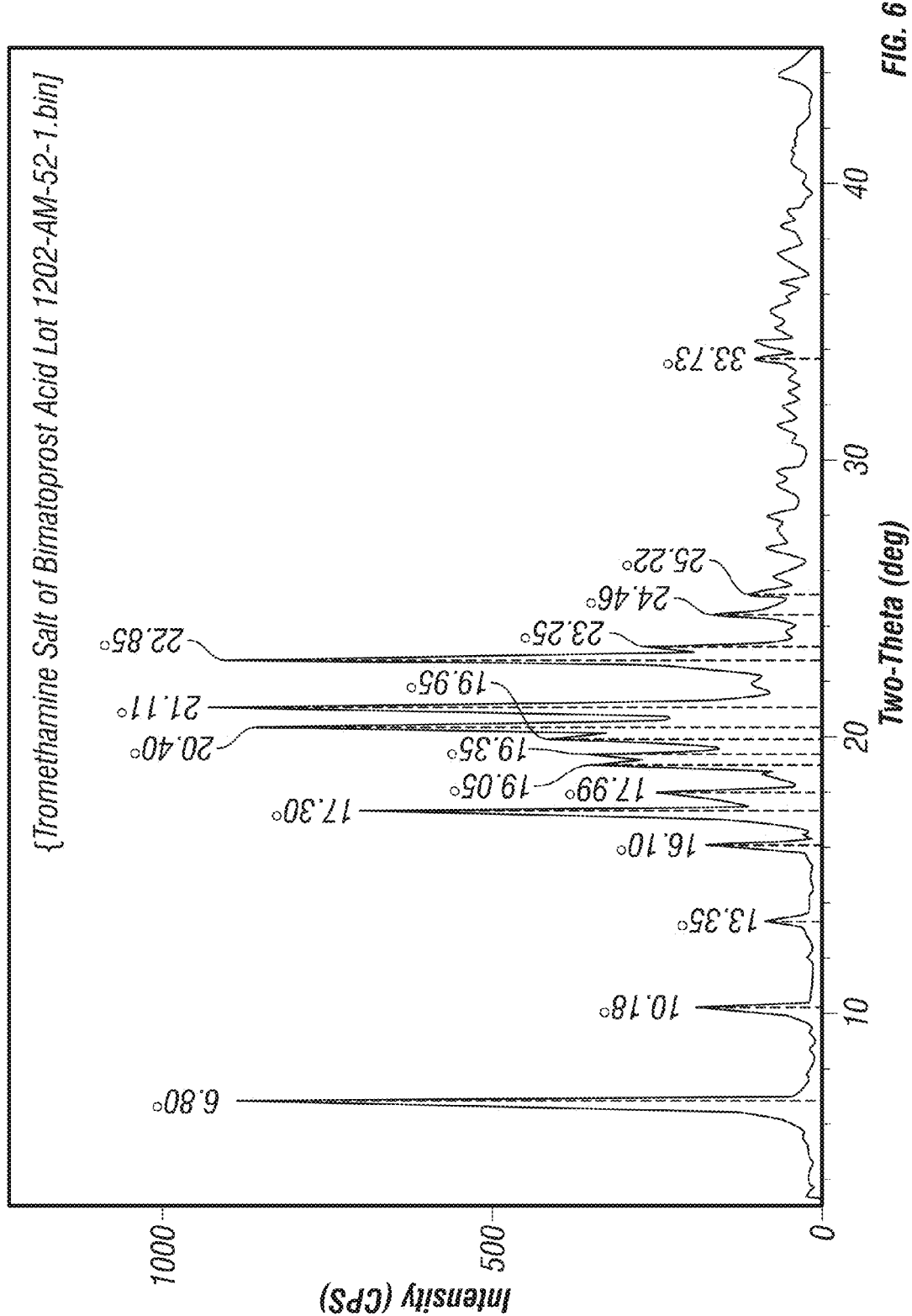
FIG. 6 shows the XRPD pattern of Tromethamine Salt of Bimatoprost Acid (Form 1) including peak positions (2-theta) for the Characteristic peaks. The data were generated by using Cu K-alpha1 radiation with wavelength 1.5406 Å.

Tromethamine salt of bimatoprost acid crystalline Form 1 was characterized using X-ray powder diffraction (XRPD), differential scanning calorimetry (DSC), ion chromatography and $^1$H NMR. The crystalline Form 1 of tromethamine salt of bimatoprost acid exhibits a distinct XRPD spectrum, which is set forth in FIG. 6. The pattern has characteristic peaks observed at 6.80°, 10.18°, 13.35°, 16.10°, 17.30°, 17.99°, 19.05°, 19.35°, 19.95°, 20.40°, 21.11°, 22.85°, 23.25°, 24.46°, 25.22° and 33.73° of 2-theta (Cu, K-alpha1 radiation with wavelength 1.5406 Å).

Figure 5:
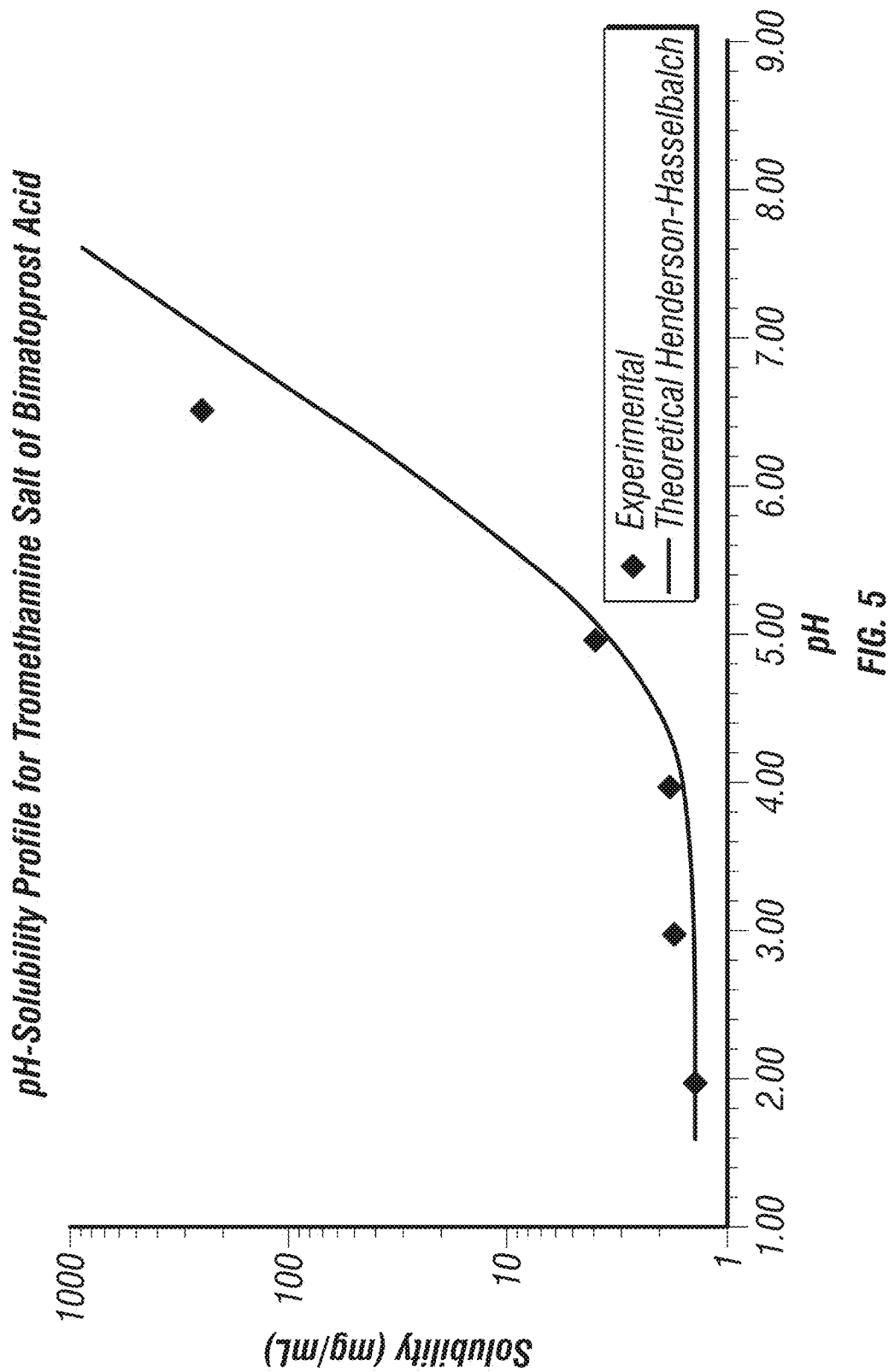
FIG. 5 shows the pH-solubility of Tromethamine Salt of Bimatoprost Acid (Form 1): the intrinsic solubility is 1.385 mg/mL at pH 2 (solubility of the free acid). Solubility of the salt at pH above 6.5 is measured as higher than 250 mg/mL (≥25 w/v %).

Tromethamine salt of bimatoprost acid of crystalline Form 1 has advantages over the crystalline free acid of bimatoprost, such as a significantly higher melting temperature (~40° C.) (see FIG. 1). This makes the tromethamine salt of bimatoprost acid of crystalline Form 1 desirable for hot melt extrusion and process manufacturing of implants and solid dosage forms, because the form does not change under these conditions. The salt (Form 1) has shown feasibility for extrusion. The salt (Form 1) was shown to be physically stable for >3 months at 25° C./60% relative humidity (RH) in open container closure, and >3 months at 40° C./75% RH in closed container closure. Furthermore, the tromethamine salt (Form 1) has a faster dissolution rate than the free acid, and a high solubility (e.g., ≥250 mg/mL at pH 6.5; see FIG. 5).

Tromethamine salt of bimatoprost acid may be prepared in crystalline Form 1 by using methods described herein. For example, tromethamine solution (1 equiv) is added to bimatoprost free acid (1 equiv), followed by the addition of water to dissolve the material. The resulting solution is rapidly frozen and freeze dried to obtain the tromethamine salt of bimatoprost acid as a lyophilized solid. After lyophilization, the salt may be in crystalline Form 1, amorphous form, or an amorphous/crystalline mixture. The lyophilized salt is then crystallized from an organic solvent, such as ethyl acetate, by subjecting the lyophilized solid sample in the organic solvent to a series of heat/cool cycles. The heat/cool cycles may include heating to about 50° C. at about 5° C./min, holding at about 50° C. for about 30 minutes, followed by cooling at about 0° C. at about 0.1° C./min, and holding at about 0° C. for about 1 hour under constant stirring. The recovered material (crystalline Form 1) is analyzed by XRPD.

In another example, tromethamine salt of bimatoprost acid in crystalline Form 1 is prepared by reacting bimatoprost free acid and tromethamine base in methanol, followed by evaporation of the methanol to dryness. Then, isopropyl alcohol is added, and the mixture is heated to about 40° C. A solid is formed after about 30 minutes. Then isopropylacetate is added at about 40° C., followed by cooling to about 20° C. and stirring for about 3 hours. The mixture is filtered to recover the tromethamine salt of bimatoprost acid in crystalline Form 1.

Pharmaceutical compositions may be prepared by combining a therapeutically effective amount of tromethamine salt of bimatoprost acid in crystalline Form 1 according to the invention, with pharmaceutically acceptable excipients, including excipients suitable for ophthalmic or dermal administration, and by preparation of unit dosage forms suitable for topical ocular or dermal use. The therapeutically efficient amount typically is between about 0.0001 and about 5% (w/v), preferably about 0.001 to about 1.0% (w/v) in liquid formulations, or preferably about 0.01 to about 0.1% w/v and 0.01% w/v to about 0.03% w/v. An "effective amount" is an amount sufficient to accomplish a stated purpose (e.g., achieve the effect for which it is administered, treat a disease, reduce one or more symptoms of a disease or improve the condition for hair growth). An example of an "effective amount" is an amount sufficient to contribute to the treatment, prevention, or reduction of a symptom or symptoms of a disease, which can be referred to as a "therapeutically effective amount." A "reduction" of a symptom or symptoms (and grammatical equivalents of this phrase) means decreasing of the severity or frequency of the symptom(s), or elimination of the symptom(s). The actual amount effective for a particular application will depend, inter alia, on the condition being treated.

The present invention provides tromethamine salt of bimatoprost acid in amorphous form.

Tromethamine salt of bimatoprost acid may be prepared in amorphous form by using methods described herein, including lyophilization, rotary evaporation, or preferably, by quenching the melt. For example, after preparing the tromethamine salt of bimatoprost acid by any of the methods described herein, including the methods described for the preparation of crystalline Form 1, the solid salt may then be heated up in a vacuum oven at about 120° C., and the temperature maintained for about 10 minutes to melt the product. The samples are quenched in air and then cooled to about −20° C. (freezer) to obtain an amorphous glass.

Pharmaceutical compositions may be prepared by combining a therapeutically effective amount of tromethamine salt of bimatoprost acid in amorphous form according to the invention, with pharmaceutically acceptable excipients, including excipients suitable for ophthalmic or dermal administration, and by preparation of unit dosage forms suitable for topical ocular or dermal use. The therapeutically efficient amount typically is between about 0.0001 and about 5% (w/v), preferably about 0.001 to about 1.0% (w/v) in liquid formulations, or preferably about 0.01 to about 0.1% w/v and 0.01% w/v to about 0.03% w/v. An "effective amount" is an amount sufficient to accomplish a stated purpose (e.g., achieve the effect for which it is administered, treat a disease, reduce one or more symptoms of a disease or improve the condition for hair growth). An example of an "effective amount" is an amount sufficient to contribute to the treatment, prevention, or reduction of a symptom or symptoms of a disease, which can be referred to as a "therapeutically effective amount." A "reduction" of a symptom or symptoms (and grammatical equivalents of this phrase) means decreasing of the severity or frequency of the symptom(s), or elimination of the symptom(s). The actual amount effective for a particular application will depend, inter alia, on the condition being treated.

EXAMPLES

Example 1

Salt Screening Studies of Bimatoprost Free Acid, and Method of Making Crystalline Form 1 of Bimatoprost Tromethamine Salt The tromethamine salt of bimatoprost acid was prepared during salt screening studies on bimatoprost free acid, where basic counter ions (both organic and inorganic) were selected based on their pKa values and suitability for pharmaceutical use.

The following salt formation techniques were used for salt screening on bimatoprost acid:

a) Lyophilization: Salts were prepared via lyophilization of aqueous solutions of bimatoprost free acid (10 mg bimatoprost acid per vial, diluted to 100 μL) and selected bases (1 molar equivalents). Bases which were supplied as liquids were added neat whereas bases which were supplied as powders were added as 1M stock solutions as described in Table 1. The solutions were rapidly frozen using dry ice in order to avoid nucleation occurring prior to lyophilization. The resulting gums or solids were analysed by $^1$H NMR to confirm salt formation.

b) Salt Formation via Direct Solvent Crystallization: For bases which were insoluble in water, the following procedure was employed. Experiments were conducted by directly adding the base (1 molar equivalent) to the bimatoprost free acid (10 mg per vial) in the crystallization solvent (100 μl). Bases which were supplied in liquid form were used directly whereas bases which were supplied as solids were added as 1M aqueous solutions. Any gums which resulted were matured for up to 10 days, and any solutions obtained were stored at 5° C. If no solid resulted, a drop of methanol was added to the gums to try and aid dissolution at 50° C., anti-solvent was added to solutions and all experiments were matured again for a further two days. Salt formation was confirmed by $^1$H NMR.

c) Salt Preparation Via Ion Exchange: A number of the bases were supplied as salts, therefore, ion exchange experiments with the sodium salt were carried out. The sodium salt was initially prepared by lyophilization. The sodium salt was then dissolved in a suitable organic solvent, specifically, IPA for the calcium and magnesium salts; dichloromethane (DCM) for tridodecylmethylammonium bromide, tetraoctylammonium bromide, and 1-α-phospatidylethanolamine; and chloroform for tetraoctadecylammonium bromide. The desired base (0.5-1 molar equivalents) was added as a stock solution, again in a suitable organic solvent (1M solution in methanol for calcium and magnesium chloride, minimum amount of DCM and a minimum amount of chloroform). In the case of the calcium and magnesium salt experiments, sodium chloride was precipitated and removed by filtration. The solvent was then allowed to evaporate to dryness leaving a gum. Equal volumes (0.5 ml) of water and diethyl ether were added and the solution shaken. Any solid formed was isolated and analysed by XRPD. The sodium chloride and sodium bromide was removed from the quaternary amine experiments by washing with water to give two layers. The aqueous layer was removed and the organic layer allowed to evaporate to dryness. The resulting gums and solids were analyzed by $^1$H NMR and XRPD.

d) Salt Formation Via Grinding: An attempt was also made to generate salts by grinding. In these experiments, 25 mg of the bimatoprost free acid and 1 molar equivalent of the base were placed in a stainless steel milling container along with a stainless steel ball and shaken horizontally for 1 minute at 25 Hz. Any solids collected were analyzed by XRPD.

Table 1 provides a summary of the bases and salt forming techniques used in small scale salt screening studies on bimatoprost acid, and the observed physical forms for the resulting solids. The majority of the counter ions resulted in crude materials that appeared as oils and gums. Surprisingly, when tromethamine was used as the base, a crystalline solid was obtained.

TABLE 1

Bases and Salt Preparation Techniques.

| Base (Source of Basic Counter Ion) | pKa | Addition Type | Salt Forming Technique | Solid Crystalline Salt Obtained |
|---|---|---|---|---|
| Tromethamine | 8.07 | Isopropyl-acetate (iPrOAc) | Lyophilization | Yes |
| Potassium | 14.00 | 2.56M solution of KOEt in EtOH | Lyophilization | No |
| Sodium | 14.00 | 2.68M solution of NaOEt in EtOH | Lyophilization | No |
| Arginine | 13.20 | 1M aq. solution | Lyophilization | No |
| Calcium | 12.70 | 1M solution of CaCl$_2$ in MeOH | Ion exchange | Partially crystalline, no stoichiometry |

TABLE 1-continued

Bases and Salt Preparation Techniques.

| Base (Source of Basic Counter Ion) | pKa | Addition Type | Salt Forming Technique | Solid Crystalline Salt Obtained |
|---|---|---|---|---|
| Magnesium | 11.40 | 1M solution of MgCl₂ in MeoH | Ion exchange | No |
| Choline | 11.00 | 50% aq. Solution | Lyophilization | No |
| Ethylenediamine | 10.09 | Neat | Lyophilization | No |
| Benzathine | 9.99 | Neat | Direct crystallization | No |
| Piperazine | 9.82 | 1M aq. Solution | Lyophilization | No |
| 2-diethylamino ethanol | 9.58 | Neat | Lyophilization | No |
| Hydroxyethyl pyrrolidine | 9.44 | Neat | Lyophilization | No |
| Ammonium hydroxide | 9.27 | Neat | Lyophilization | No |
| Dimethylamino ethanol | 8.83 | Neat | Lyophilization | No |
| N-ethyl-glucamine | 8.03 | 1M aq. Solution | Lyophilization | No |
| N-methyl-glucamine | 8.03 | 1M aq. Solution | Lyophilization | No |
| Hydroxyethyl-morpholine | 7.39 | Neat | Lyophilization | No |
| Citrulline | 7.00 | 1M aq. Solution | Direct crystallization | No |
| Benethamine | 4.46 | Neat | Direct crystallization | No |
| Tridodecyl-methyl-ammonium chloride | — | Minimum amount of DCM | Ion exchange | No |
| Tetraoctyl-ammonium bromide | — | Minimum amount of DCM | Ion exchange | No |
| Tetraoctadecyl-ammonium bromide | — | Minimum amount of CHCl₃ | Ion exchange | No |
| L-α-Phosphatidyl-ethanolamine, dioleoyl | — | Minimum amount of DCM | Direct crystallization | No |

Figure 1:
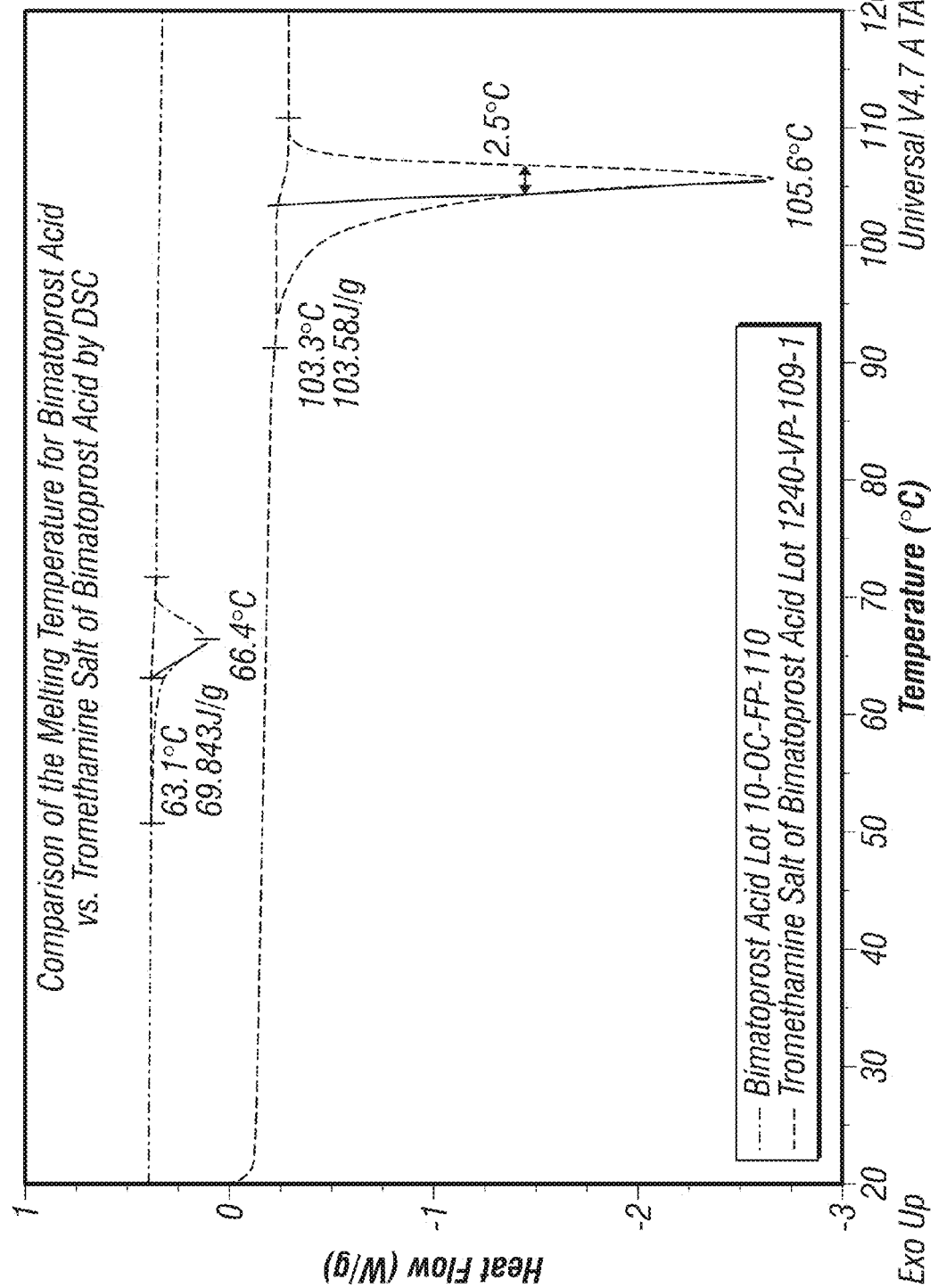
FIG. 1 depicts DSC data for Bimatoprost Acid (crystalline anhydrous) (top trace) compared to the Tromethamine Salt of Bimatoprost Acid (crystalline Form 1) (bottom trace), showing a melting temperature for the salt at about 40° C. higher than the melting temperature of the free acid.

The tromethamine salt of bimatoprost acid obtained as described above was analyzed by XRPD, DSC, and $^1$H NMR. The melting temperature of the tromethamine salt (105.6° C.) was significantly higher than melting temperature of the free acid (66.4° C.), as determined by DSC (FIG. 1). The formation of the tromethamine salt was confirmed by $^1$H-NMR and ion chromatography, which confirmed the structure of the molecule and a 1:1 ratio of the acid and the counter ion. It was concluded that bimatoprost acid tromethamine salt was a pure crystalline salt suitable for pharmaceutical development.

In a first scale up procedure, the preparation and crystallization of the tromethamine salt of bimatoprost acid (Form 1) was conducted on about 100 mg scale. To bimatoprost free acid (100 mg) was added 1 equivalent of base (tromethamine) as a 1M aqueous solution (254 μl). Water (2 ml) was added to dissolve the material and then the solution was rapidly frozen and freeze dried to obtain the tromethamine salt as a lyophilized solid. The salt was then crystallized from ethyl acetate as follows. The lyophilized solid sample in ethyl acetate was subjected to initial heat/cool cycles using an Anachem React-Array. The sample was then subjected to three heat/cool cycles by using the following procedure: heating to 50° C. at 5° C./min, holding at 50° C. for 30 minutes, followed by cooling to 0° C. at 0.1° C./min, holding at 0° C. for 1 hour under constant stirring at 500 rpm. The recovered material (crystalline form 1) was analyzed by XRPD (FIG. 6), $^1$H NMR, thermal analysis, and gravimetric vapor sorption (GVS) analysis, as summarized in Table 2.

TABLE 2

Characterization of Tromethamine Salt of Bimatoprost Acid (Form 1)

| Technique | Results |
|---|---|
| XRPD | Crystalline Form 1 (FIG. 6) |
| $^1$H NMR | Consistent with structure Stoichiometry 1.0:1.0 (Parent:Counter ion) |
| Thermal Analysis | TGA: Loss of 1.0% w/w from 40° C. to 150° C. (Process solvent). Loss of 25.4% w/w from 150° C. to 350° C. (possible salt dissociation, theoretical value for the loss of tromethamine: 23.7% w/w). DSC: melting onset at 104-110° C. (ΔHf = 103 to 119 J/g). |
| GVS analysis | 90% RH, no deliquescence, no hydrate formed. |

In another scale-up procedure, tromethamine salt of bimatoprost acid (crystalline Form 1) was prepared at multi-gram scale by using the following procedure.

Bimatoprost free acid was reacted with tromethamine base in methanol, followed by the evaporation of the methanol to dryness. Then isopropyl alcohol (IPA) was added, and the mixture was heated to 40° C. No seeding was required. A solid was formed within 30 minutes. Then, isopropylacetate (iPrOAc) was added at 40° C., then cooled to 20° C. and stirred for 3 hours, and then filtered to recover the tromethamine salt of bimatoprost acid (Form 1) in ~85%. The XRPD pattern of the recovered salt was consistent with crystalline Form 1 shown in FIG. 6, confirming that the multigram scale-up procedure generated crystalline Form 1.

Figure 2:
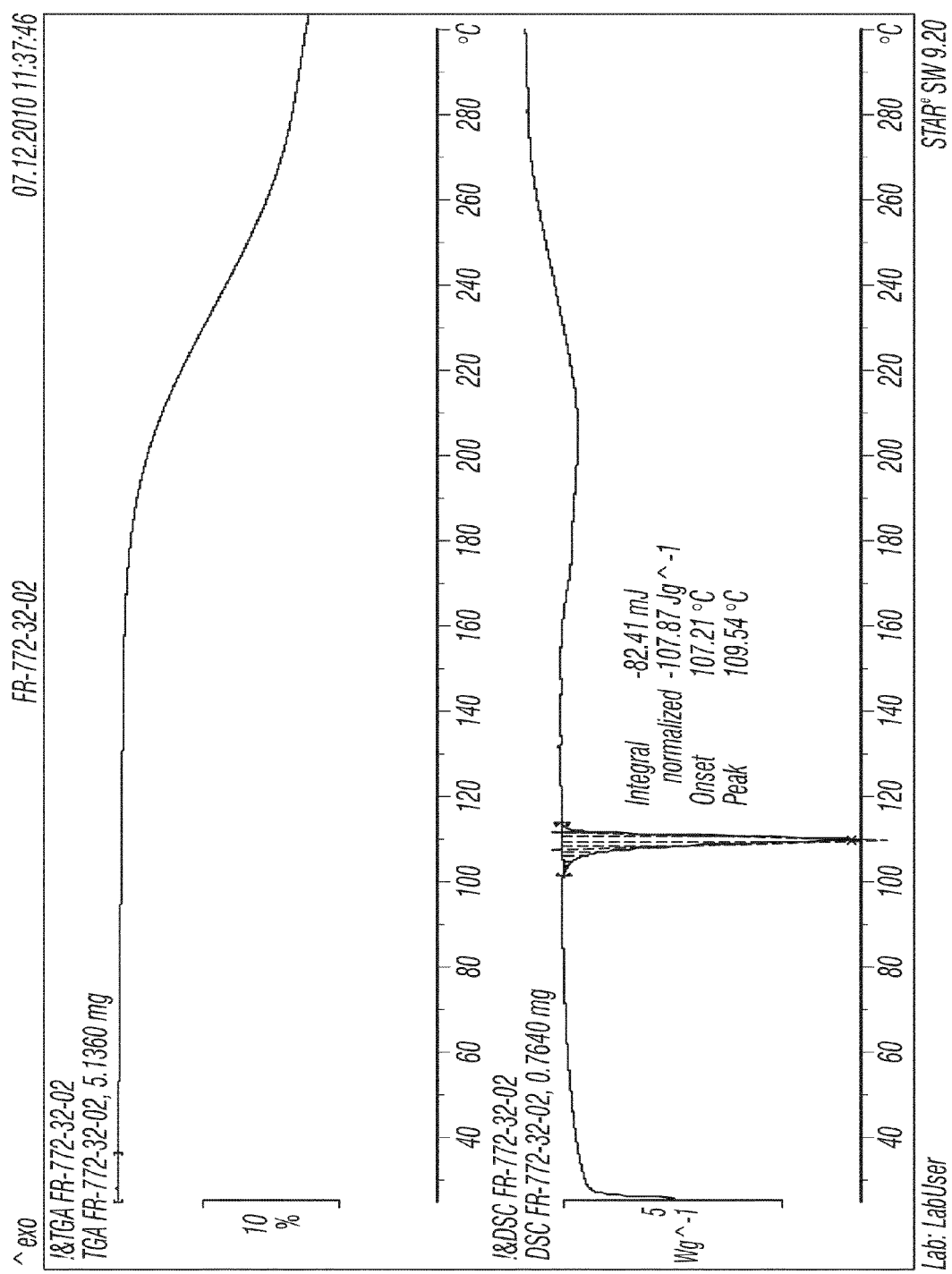
FIG. 2 depicts DSC/TGA analyses of Tromethamine Salt of Bimatoprost Acid (Form 1), showing that the tromethamine salt of bimatoprost acid melted at about 107.2° C. (bottom trace) followed by a weight loss at a temperature greater than the melting temperature of the salt (top trace).
Figure 3:
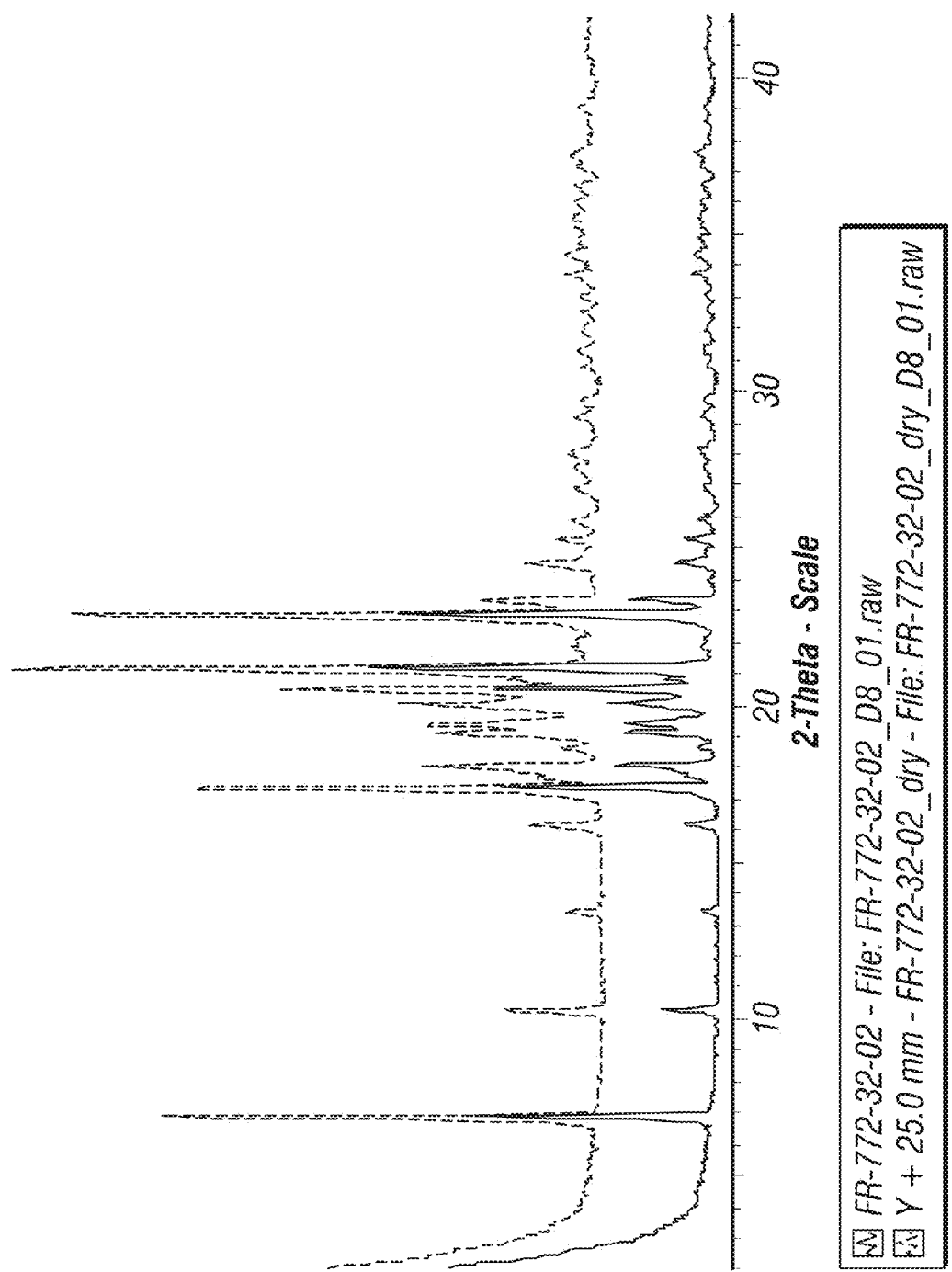
FIG. 3 depicts XRPD patterns of Tromethamine Salt of Bimatoprost Acid (Form 1) before (bottom trace) and after (top trace) drying process.
Figure 4:
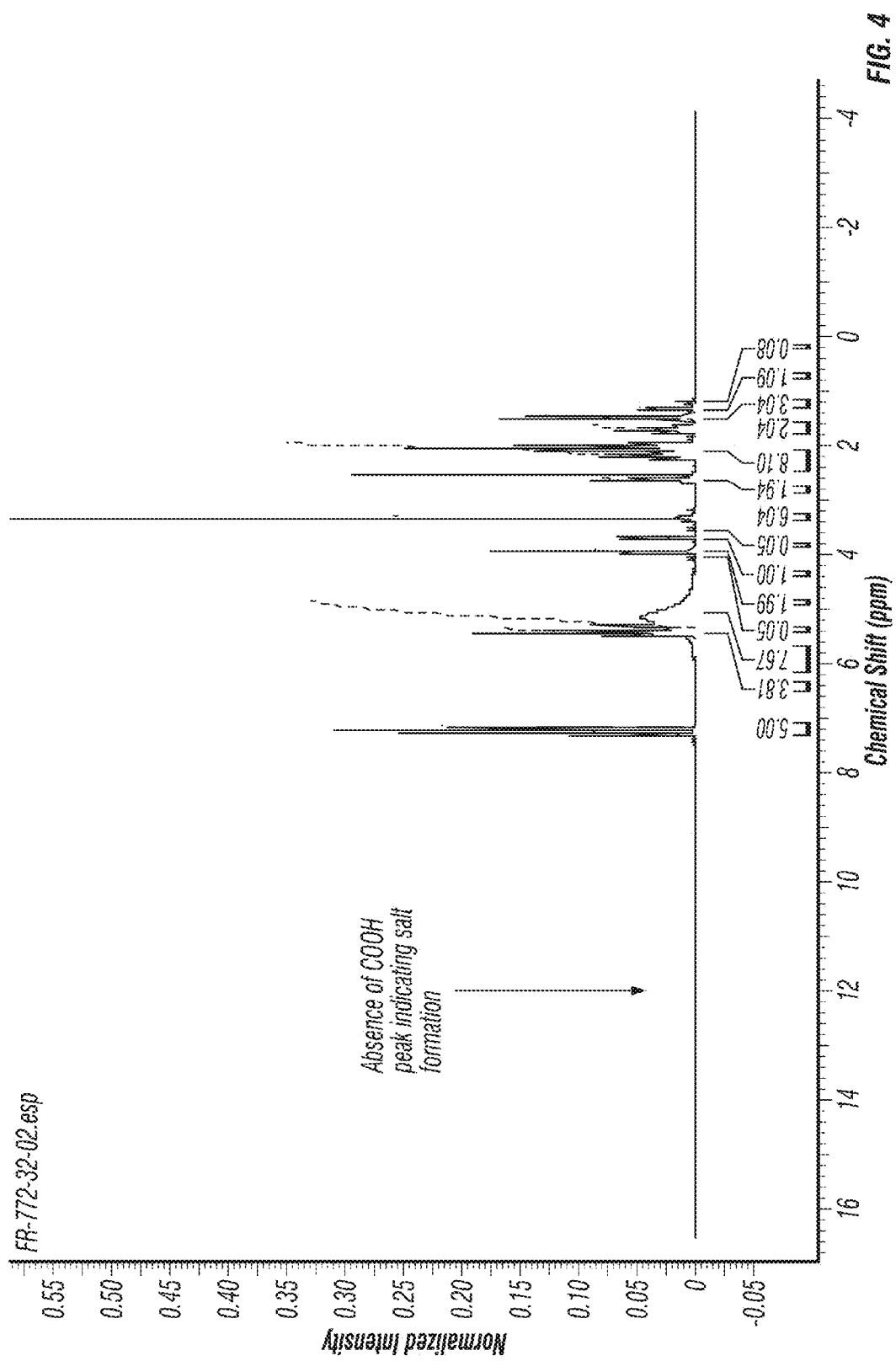
FIG. 4 shows the $^1$H NMR of Tromethamine Salt of Bimatoprost Acid (Form 1, dissolved in DMSO-d6). The absence of the $^1$H NMR peak for the —COOH proton at about 12 ppm indicates formation of the salt.

When stored at or above 80% RH, tromethamine salt of bimatoprost acid behaves hygroscopically, with significant moisture uptake observed. Without being bound by any particular theory, the significant uptake of moisture may be a result of the large specific surface area of the material. On desorption, the adsorbed water was rapidly lost with no equilibrium established. At the end of the gravimetric vapor sorption (GVS) cycle, at 40% RH, the overall sample mass increased by 5 wt %. XRPD re-analysis of the sample post GVS analysis showed no change in the crystalline Form 1 (FIG. 3). Thermal analyses by TGA and DSC showed that the tromethamine salt of bimatoprost acid melted at about 107.2° C. followed by a weight loss (FIG. 2).

Example 2

Method of Making the Amorphous Form of Tromethamine Salt of Bimatoprost Acid

Attempts were made to prepare amorphous tromethamine salt of bimatoprost acid by freeze drying (using a mixture of tert-butanol/water (50/50 v/v) as solvent), rotary evaporation, and by quenching the melt. Quenching the melt was selected as a suitable method for the preparation of the amorphous material, followed by characterization.

In one experiment, Tromethamine Salt of Bimatoprost acid (prepared as described in Example 1) was heated in a vacuum oven at 120° C., the temperature was maintained for 10 minutes to melt the product. The samples were quenched in air and then cooled to −20° C. (freezer) to obtain an amorphous glass. The glass transition (Tg) was determined as about 29° C. by modulated differential scanning calorimetry (MDSC).

Figure 7:
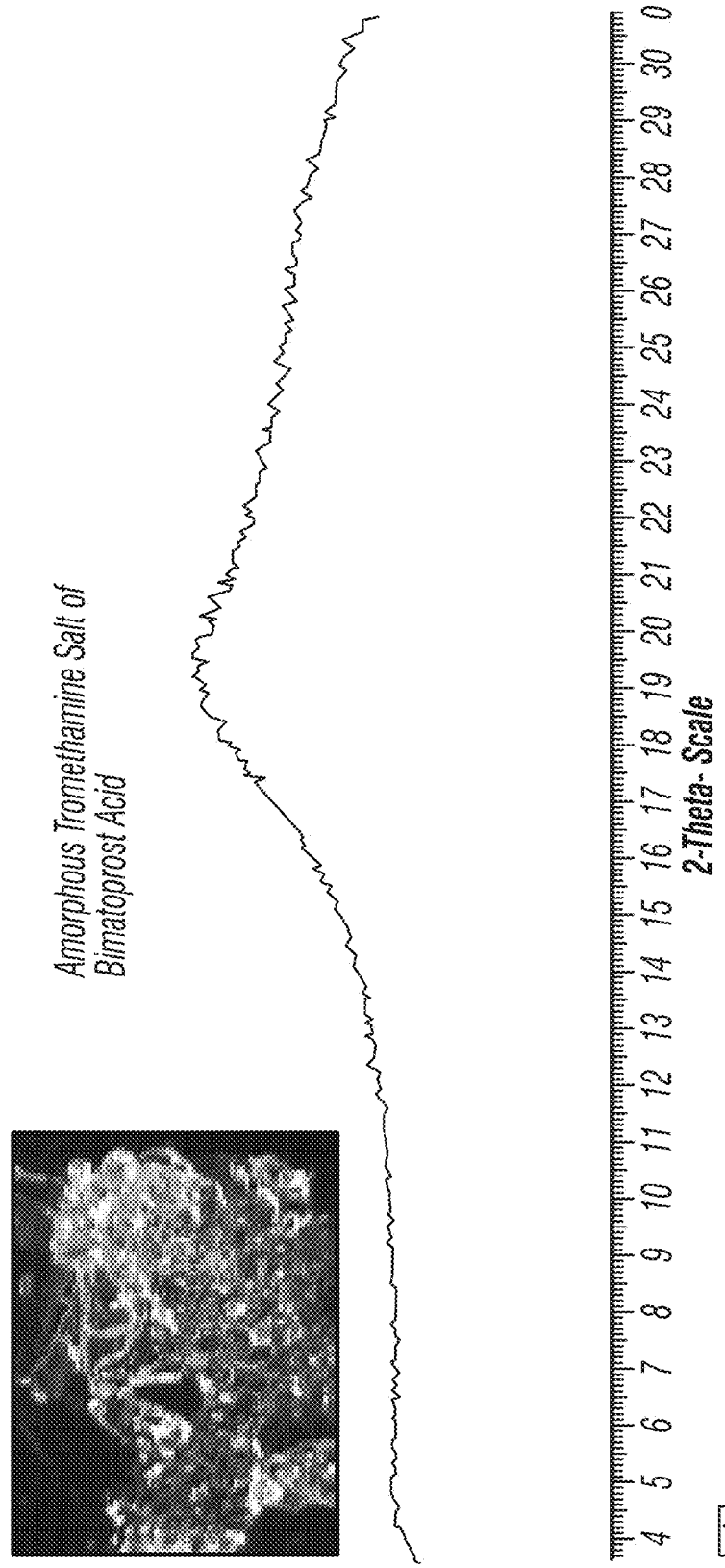
FIG. 7 shows the XRPD pattern and microscopy of amorphous Tromethamine Salt of Bimatoprost Acid with its characteristic halo.
Figure 8:
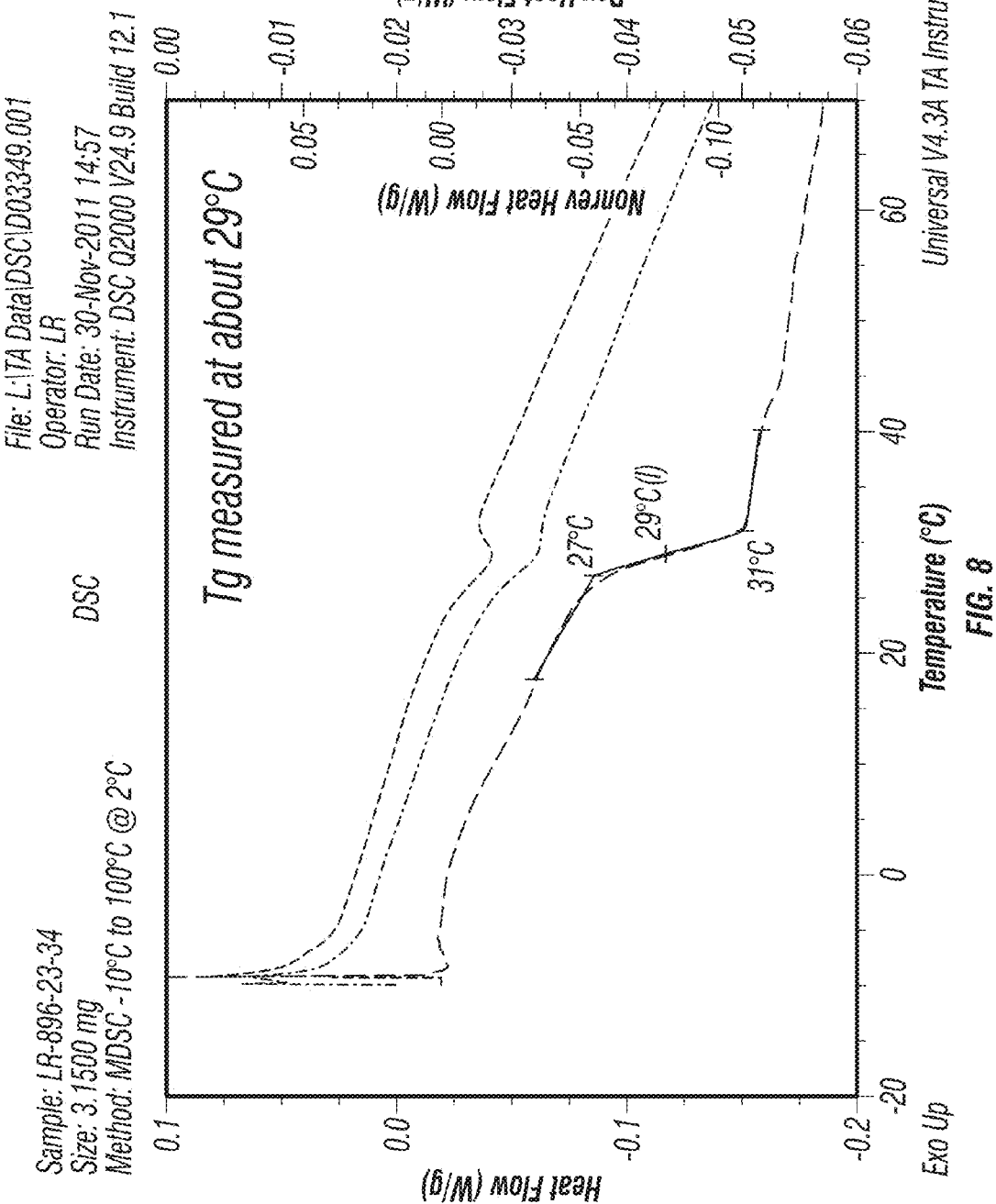
FIG. 8 shows Modulated differential scanning calorimetry (MDSC) of Amorphous Tromethamine Salt of Bimatoprost Acid. Reversed Heat Flow data (the lower curve) is indicating a glass transition temperature for the amorphous form at 29° C. (midpoint of the baseline shift).

Characterization of Amorphous Tromethamine Salt of Bimatoprost Acid:

The characterization of the prepared amorphous material is summarized in Table 3. The broad X-ray powder diffraction pattern obtained from the amorphous material showed a continuous intensity distribution indicative of an amorphous form, consisting of a non-crystalline phase material (see FIG. 7). The $^1$H NMR spectrum was consistent with the expected structure, therefore, no measurable degradation or dissociation of the produced salt was observed. The glass transition of the amorphous material of Bimatoprost Acid Tromethamine Salt was determined as approximately 29° C. by the modulated differential calorimetry (MDSC); no re-crystallization was observed on further heating up to 100° C.

TABLE 3

Characterization of Amorphous Bimatoprost Acid Tromethamine Salt

| Compound | Bimatoprost Acid Tromethamine Salt |
|---|---|
| Preparation Method | Quenching the melt |
| XRPD | Amorphous |
| $^1$H-NMR | Consistent with structure. Stoichiometry 1.0:1.0 (Parent:Counterion) |
| MDSC | Tg at about 29° C. |

I. Instrument and Methodology Details

A. X-Ray Powder Diffraction (XRPD)

X-Ray Powder Diffraction patterns were collected on a Bruker D8 diffractometer using Cu and anode (40 kV, 40 mA) as the X-ray source that generates K$\alpha$1 radiation with a wavelength of 1.5406 Å, theta/2-theta goniometer, and divergence of V4 and receiving slits, a Ge monochromator and a Lynxeye detector. The instrument was performance checked using a certified Corundum Standard (NIST 1976). The software used for data collection was Diffrac Plus XRD Commander v2.6.1 and the data were analyzed and presented using Diffrac Plus EVA v13.0.0.2 or v15.0.0.0.

Samples were run under ambient conditions as flat plate specimens. The solid sample was gently packed into a cavity cut into a polished, zero-background (510) silicon wafer. The sample was rotated in its own plane during analysis. The details of the data collection are:

Angular range: 2 to 42° (2-theta);
Step size: 0.05° (2-theta); and,
Collection time: 0.5 sec./step.

B. Nuclear Magnetic Resonance (NMR):

$^1$H NMR spectra were collected on a Bruker 400 MHz instrument equipped with an auto-sampler and controlled by a DRX400 console. Automated experiments were acquired using ICON NMR v4.0.4 running with Topspin v1.3 using the standard Bruker loaded experiments. For non-routine spectroscopy, data were acquired through the use of Topspin alone. Samples were prepared in DMSO-d$_6$, unless otherwise stated. Off-line analysis was carried out using Topspin v1.3 or ACD SpecManager v12.5.

C. Differential Scanning Calorimetry (DSC):

DSC data were collected on a TA Instruments Q2000 equipped with a 50 position autosampler. The calibration for thermal capacity was carried out using sapphire and the calibration for energy and temperature was carried out using certified indium. Typically 3 to 3.5 mg of each sample, in an aluminum pan, was heated at 10° C./min from 25° C. to 130° C. A purge of dry nitrogen at 50 ml/min was maintained over the sample.

Modulated temperature DSC ("MDSC") was carried out using an underlying heating rate of 2° C./min and temperature modulation parameters of ±0.318° C. (amplitude) every 60 seconds (period). The instrument control software was Advantage for Q Series v2.8.0.394 and Thermal Advantage v5.2.6 and the data were analyzed using Universal Analysis v4.7A or v4.4A.

D. Thermo-Gravimetric Analysis (TGA):

TGA data were collected on a Mettler TGA/SDTA 851e equipped with a 34-position autosampler. The instrument was temperature calibrated using certified indium. Typically, 5 to 30 mg of each sample was loaded onto a pre-weighed aluminum crucible and was heated at 10° C./min from ambient temperature to 350° C. A nitrogen purge at 50 mL/min was maintained over the sample. The instrument control and data analysis software was STARe v9.20.

E. Ion Chromatography (IC):

Data were collected on a Metrohm 761 Compact IC using IC Net software v2.3. Accurately weighed samples were prepared as stock solutions in an appropriate dissolving solution and diluted appropriately prior to testing. Quantification was achieved by comparison with standard solutions of known concentration of the ion being analysed.

TABLE 4

IC Method Parameters for Cation Chromatography

| Type of method | Cation exchange |
|---|---|
| Column | Metrosep C 2 – 250 (4.0 × 250 mm) |
| Column Temperature (° C.) | Ambient |
| Injection volume (μl) | 20 |
| Detection | Conductivity detector |
| Flow Rate (ml/min) | 1.0 |
| Eluent | 4.0 mM Tartaric acid, 0.75 mM Dipicolinic acid in 5% aqueous acetone |

F. pH-Solubility Determination:

The pH solubility profile for tromethamine salt of bimatoprost acid of Form 1 was determined by suspending a sufficient amount of the compound in aqueous media, then placing on a shaker at 25° C., 750 rpm for 48 hrs. The pH was checked, and adjusted if necessary, at intervals of 1, 5, 23, 28 and 47 hrs. An aliquot of sample was taken off at 24 hrs and the final pH was recorded. The suspension was then filtered through a glass fiber C filter. The filtrate was then diluted by an appropriate factor. This was repeated at 48 hours. Quantitation was by HPLC with reference to 6 standard solutions of concentrations between 0.3873-0.0008 mg/ml dissolved in 66:21:13 H$_2$O:ACN:MeOH. The solubility vs. pH plot (FIG. 5) was fit to the theoretical relationship presented Henderson-Hasselbalch equation: S=So (1+10^(pH−pKa)) for the free acid by using the measured pKa of 4.76 for bimatoprost acid.

G. Ophthalmic Preparations:

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water. The pharmaceutical compositions of the present invention may include a surfactant; however, surfactants are not necessary as surfactants are added to formulations to dissolve or increase solubility of the drug in formulation vehicles. In case of tromethamine salt, the solubility is high enough (~25 w/v % at pH 6.8) so that no surfactant is needed.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

Ingredient Amount (% w/w) active ingredient about 0.001-5 preservative, 0-0.10 vehicle, 0-40 tonicity adjustor, 0-10 buffer, 0.01-10 pH adjustor, q.s. pH 4.5-7.5, antioxidant as needed, surfactant as needed, purified water as needed to make 100%.

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for drop-wise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 µl.

While this invention has been described with respect to these specific examples, it is understood that other modifications and variations are possible without departing from the spirit of the invention.

What is claimed is:

1. A method for localized fat reduction comprising administering to a subject in need thereof a therapeutically effective amount of a crystalline form of the tromethamine salt of bimatoprost acid in an pharmaceutically acceptable carrier, wherein the crystalline form of the tromethamine salt of bimatoprost acid has an X-ray powder diffraction pattern with peaks at 6.80°, 10.18°, 13.35°, 16.10°, 17.30°, 17.99°, 19.05°, 19.35°, 19.95°, 20.40°, 21.11°, 22.85°, 23.25°, 24.46°, 25.22° and 33.73° of 2-theta (Cu, K-alpha1 radiation with wavelength 1.5406 Å).

2. A method for promotion of hair growth comprising administering to a subject in need thereof a therapeutically effective amount of a crystalline form of the tromethamine salt of bimatoprost acid an pharmaceutically acceptable carrier, wherein the crystalline form of the tromethamine salt of bimatoprost acid has an X-ray powder diffraction pattern with peaks at 6.80°, 10.18°, 13.35°, 16.10°, 17.30°, 17.99°, 19.05°, 19.35°, 19.95°, 20.40°, 21.11°, 22.85°, 23.25°, 24.46°, 25.22° and 33.73° of 2-theta (Cu, K-alpha1 radiation with wavelength 1.5406 Å).

* * * * *

UNITED STATES PATENT AND TRADEMARK OFFICE
CERTIFICATE OF CORRECTION

PATENT NO. : 10,273,206 B2
APPLICATION NO. : 14/318402
DATED : April 30, 2019
INVENTOR(S) : Thomas K. Karami et al.

Page 1 of 1

It is certified that error appears in the above-identified patent and that said Letters Patent is hereby corrected as shown below:

In the Specification

In Column 12, Line 12, delete "phospatidylethanolamine;" and insert -- phosphatidylethanolamine; --, therefor.

In the Claims

In Column 18, Line 26, in Claim 1, delete "an" and insert -- a --, therefor.

In Column 18, Line 36, in Claim 2, after "acid" insert -- in -- and delete "an" and insert -- a --, therefor.

Signed and Sealed this
Thirty-first Day of December, 2019

Andrei Iancu
*Director of the United States Patent and Trademark Office*